(12) United States Patent
Ledbetter

(10) Patent No.: US 8,735,648 B2
(45) Date of Patent: May 27, 2014

(54) **MODEL SYSTEM OF *ACANTHAMOEBA* KERATITIS SYNDROME AND METHOD FOR SELECTING A TREATMENT THEREOF**

(75) Inventor: Eric Ledbetter, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/576,313

(22) PCT Filed: Feb. 8, 2011

(86) PCT No.: PCT/US2011/024002
§ 371 (c)(1),
(2), (4) Date: Oct. 2, 2012

(87) PCT Pub. No.: WO2011/097609
PCT Pub. Date: Aug. 11, 2011

(65) Prior Publication Data
US 2013/0031646 A1    Jan. 31, 2013

Related U.S. Application Data

(60) Provisional application No. 61/302,258, filed on Feb. 8, 2010.

(51) Int. Cl.
*A01K 67/00* (2006.01)
*A61K 49/00* (2006.01)
*C12Q 1/68* (2006.01)
*G01N 33/53* (2006.01)
*C12Q 1/02* (2006.01)

(52) U.S. Cl.
USPC ............... 800/9; 424/9.2; 435/6.12; 435/7.1; 435/29

(58) Field of Classification Search
CPC ................................................ A01K 2207/20
See application file for complete search history.

(56) References Cited

U.S. PATENT DOCUMENTS

| 6,773,916 | B1 | 8/2004 | Thiel et al. |
| 2003/0113822 | A1 | 6/2003 | Westwood et al. |
| 2007/0140897 | A1 | 6/2007 | Wang |
| 2008/0119483 | A1 | 5/2008 | Beverley et al. |
| 2008/0249051 | A1 | 10/2008 | Roberts et al. |

FOREIGN PATENT DOCUMENTS

GB         2333609 A        7/1999

OTHER PUBLICATIONS

Naisse et al. (Investigative Ophthalmology & Visual Science, vol. 30, No. 8, Aug. 1989).*
von Bomhard et al (American Journal of Veterinary Research, Nov. 2003, vol. 64, No. 11, pp. 1421-1428).*
Ithoi et al. (Tropical Biomedicine. 2013; 30(1): 131-140).*
Davidson et al. "A Feline Model of Ocular Toxoplasmosis," Investigative Opthamology & Visual Science, 34(13), 3653-3660.
Hurt et al. "Exacerbation of *Acanthamoeba* Keratitis in Animals Treated with Anti-Macrophage Inflammatory Protein 2 or Antineutrophil Antibodies," Infection and Immunity, 69(5), 2988-2995.
Klink et al., "The Role of Contact Lenses, Trauma and Langerhans Cells in a Chinese Hamster Model of *Acanthamoeba* Keratitis," Investigative Opthamology & Visual Science, 34(6), 1937-1944.
International Search Report dated Apr. 12, 2011 for PCT/US11/24002 filed on Feb. 8, 2011, entitled Model System of *Acanthamoeba* Keratitis Syndrome and Method for Selecting a Treatment Thereof.

* cited by examiner

*Primary Examiner* — Scott Long
(74) *Attorney, Agent, or Firm* — Burns & Levinson LLP; Jacob N. Erlich; Shahid Hasan

(57) ABSTRACT

Methods for generating a feline model for ocular complications arising from amoeba infection are described. The invention further relates to screening methods for therapeutics for the treatment of ocular complications using the feline model referenced to above.

10 Claims, 11 Drawing Sheets

MODEL SYSTEM OF *ACANTHAMOEBA* KERATITIS SYNDROME AND METHOD FOR SELECTING A TREATMENT THEREOF

CROSS REFERENCE TO RELATED APPLICATIONS

This application is the U.S. national phase entry under 35 U.S.C. §371 of International Patent Application No, PCT/US11/24002 filed on Feb. 8, 2011, entitled "MODEL SYSTEM OF ACANTHAMOEBA KERATITIS SYNDROME AND METHOD FOR SELECTING A TREATMENT THEREOF," which in turn claims priority of U.S. Provisional Application Ser. No. 61/302,258, filed on Feb. 8, 2010, both of which are incorporated by reference herein in their entirety for all purposes.

FIELD OF INVENTION

The present invention is related generally to the field of animal models of diseases. More particularly, the present invention is related to an animal model of *Acanthamoeba* keratitis syndrome.

BACKGROUND OF THE INVENTION

*Acanthamoeba* keratitis is a painful, vision-threatening corneal infection caused by pathogenic environmental amoebae. *Acanthamoeba* spp. are free-living opportunistic protozoa pathogens that are ubiquitous in many diverse environments including air, soil, freshwater, seawater, tap water, bottled water, swimming pools, sewage, and vegetables. Corneal infection with *Acanthamoeba* spp. was first described in humans during the mid-1970's. Since this time, dramatic increases in the number of human cases have been reported and *Acanthamoeba* keratitis is now widely recognized as an emerging ocular surface infection.

The frequency of *Acanthamoeba* keratitis is continuing to increase in many countries, including the United States, as a result of an expanding population of individuals at risk for infection, enhanced recognition of infection, improvements in diagnostic techniques, and sporadic outbreaks of infection associated with alterations of contact lens wear, contact lens handling, and water quality. The true incidence of *Acanthamoeba* keratitis is not currently known and varies widely among different geographical regions; however, recent estimates include 1 case per 30,000 hydrogel contact lens wearers per year in Europe, England, and Hong Kong; 1 case per 10,000 contact lens wearers per year in the United States; and 1 case per 4,200 outpatient visits to tertiary referral hospitals in Australia.

*Acanthamoeba* keratitis most commonly occurs in immunocompetent, healthy individuals and the most important and prevalent risk factors are contact lens wear, corneal trauma, and exposure to contaminated water or soil. *Acanthamoeba* trophozoites and cysts are capable of firmly adhering to soft contact lenses, a characteristic that explains the strong association between contact lens wear and infection. The clinical features of *Acanthamoeba* keratitis are diverse and non-specific. Corneal epithelial irregularities, epithelial ulcers, stromal infiltrates, stromal ulcers, radial keratoneuritis, and keratomalacia are common. These clinical features mimic infection with bacteria, viruses, and fungi; and amoebic keratitis is often initially misdiagnosed clinically. The diagnosis of *Acanthamoeba* keratitis is based upon demonstration of the organism or its nucleic acid with culture, cytology, histopathology, PCR, or in vivo corneal confocal microscopy.

Treatment of *Acanthamoeba* keratitis is lengthy and difficult, as few agents are effective at eliminating the cyst stage of *Acanthamoeba* within corneal tissues. Various therapeutic agents, including the diamidines, biguanides, imidazoles, and aminoglycosides have been reported with variable treatment results. Adverse ocular reactions attributable to the toxic properties of these compounds occur frequently. Treatment is often continued for a year or more and infection recurrences may develop after apparently successful medical therapy. Therapeutic keratoplasty has been used to manage acute complications associated with *Acanthamoeba* keratitis, but with generally poor results attributable to graft rejection and extension of *Acanthamoeba* infection into the graft. Therapeutic keratoplasty to resolve corneal scarring and astigmatism performed following a course of medical anti-amoebic therapy is associated with an improved surgical prognosis; however, exacerbation of ocular inflammation and graft infection still occur frequently.

The prognosis for *Acanthamoeba* keratitis is affected by severity of disease on presentation and the interval between the onset of symptoms and the start of appropriate therapy. Outcomes in the largest series of patients with *Acanthamoeba* keratitis reported that 11% of patients will require therapeutic keratoplasty, 6% require cataract surgery for complications associated with the infection or its therapy, and 2% require enucleation. Greater than 30% of patients completing treatment have 6/9 or poorer visual acuity, with 4% having only light perception or complete blindness.

The principal challenge for improving outcomes of patients with *Acanthamoeba* keratitis is the development of more effective drugs for the treatment and elimination of *Acanthamoeba* cysts within corneal tissues. Additionally, the pathogenesis of *Acanthamoeba* keratitis remains incompletely understood and the relative contribution of *Acanthamoeba* and host-derived factors in inducing tissue destruction is not clear. A major obstacle to improved understanding and treatment of *Acanthamoeba* keratitis is the lack of an appropriate animal model for comparative study. *Acanthamoeba* keratitis has been experimentally induced in pigs, rats, and Chinese hamsters; however, no spontaneous amoeba corneal infections have been identified in these animal species and the models have only been used on a limited basis since their publication. These animal models of *Acanthamoeba* keratitis develop ocular lesions that are clinically dissimilar from that of humans, require extensive host manipulation to induce infection, and possess ocular anatomy and physiology that is markedly different than humans. An improved animal model of *Acanthamoeba* keratitis would dramatically assist research efforts.

The suitability of an animal model of an ocular infectious disease is typically determined by considering four variables: 1) the animal's possession of anatomical and physiological characteristics consistent with the needs of the experiment and similar to the host being studied, 2) the presence of a naturally-occurring disease state in the species similar to the condition being studied, 3) cost and difficulty of acquiring and maintaining the animal species, and 4) availability of microbiologically defined animals for the infection of interest. The pig, rat, and hamster models of *Acanthamoeba* keratitis each fail to satisfy at least 2 of the criteria necessary for an optimal ocular infectious disease model. The pig, rat, and hamster models require extensive experimental host manipulation to establish *Acanthamoeba* infection and result in clinical ocular disease dissimilar to that observed in humans. The small globe size of rats and hamsters is difficult to examine in vivo and experimentally manipulate. Pigs are potentially dangerous to handle, expensive, and difficult to maintain.

SUMMARY OF THE INVENTION

In contrast to previously developed animal models, the first naturally-acquired *Acanthamoeba* keratitis syndrome in an animal species, namely the domestic cat, has been identified. The naturally-acquired *Acanthamoeba* keratitis is associated with clinical lesions that are almost identical to humans with *Acanthamoeba* keratitis making the domestic cat an ideal animal model for this condition. In addition to possessing ocular sizes, dimensions, and physiology that are very similar to humans, cats are relatively inexpensive and easy to maintain and specific pathogen-free laboratory cats are readily available.

The present invention provides for an animal model system of *Acanthamoeba* keratitis syndrome which is predictive of a similar syndrome in humans. In one embodiment of the invention the animal model system comprises an animal from the Felidae family. In a further embodiment the animal is a domestic cat.

The present invention also provides for a method for generating an animal model system of *Acanthamoeba* keratitis syndrome. The method comprises selecting a group of animals, and separating the group into a first subgroup and a second subgroup. The method further comprises inducing *Acanthamoeba* keratitis in the first subgroup, and selecting infected animals from the first subgroup by comparing them to the animals from the second subgroup. The *Acanthamoeba* keratitis syndrome of the method is predictive of a similar syndrome in humans.

The present invention further provides a method for selecting a therapeutic composition for treating *Acanthamoeba* keratitis syndrome. The method comprises selecting a model system of *Acanthamoeba* keratitis syndrome. The model system comprises experimental animals selected from the Felidae family, for example the domestic cat, and infecting the experimental animals with *Acanthamoeba* to induce *Acanthamoeba* keratitis. Control animals are not induced. The method further comprises administering a therapeutic composition to the experimental animals and selecting the therapeutic composition as a candidate for treating *Acanthamoeba* keratitis syndrome if the therapeutic composition is effective to cause a statistically significant reduction of the symptoms of *Acanthamoeba* keratitis syndrome or level of infection of *Acanthamoeba* species in the experimental animals as compared with said control animals.

The present invention also provides a method for screening a therapeutic compound for ameliorating or treating a symptom for *Acanthamoeba* induced complication comprising (a) providing a test animal and a substantially identical control animal wherein the test and control animal are substantially identically infected with a pathogenic amoeba (e.g., *A. castellanii*), (b) administering the therapeutic compound to the test animal, (c) maintaining the test animal and the control animal under conditions appropriate for development of at least one *Acanthamoeba* induced complication in the control animal; (d) assessing said at least one *Acanthamoeba* induced complication in the test animal and the control animal; and, (e) comparing the severity and/or onset of the *Acanthamoeba* induced complication in the test animal with that of the control animal, wherein reduced severity and/or delay in the onset of the *Acanthamoeba* induced complication in the test animal indicates that the candidate agent is the therapeutic agent useful for treating or preventing the *Acanthamoeba* induced complication.

DETAILED DESCRIPTION OF THE INVENTION

Figure 1:
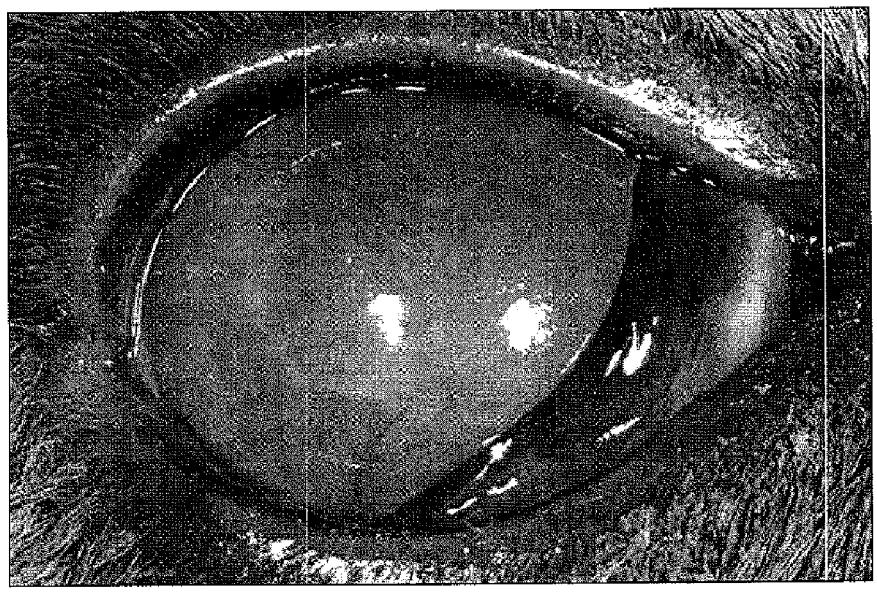
FIG. 1 shows clinical photograph of a cat with naturally-acquired *Acanthamoeba* keratitis. Corneal vascularization, edema, and a stromal ring infiltrate are present.

For an animal to serve as a useful model, the disease or pathology in the animal model has to be similar in etiology and function to the human equivalent disease or pathology. As different animals display different similarities and dissimilarities to humans, care should be taken in selecting the appropriate animal model for a specific human disease.

Accordingly, in one embodiment, the present invention provides an animal model for an *Acanthamoeba* induced ocular complication, viz., *Acanthamoeba* keratitis, in a member of the felidae family (viz., a cat) in which the *Acanthamoeba* induced ocular complication is associated with clinical lesions that are substantially identical to humans.

In one aspect, the invention is directed to the first identified naturally-acquired *Acanthamoeba* keratitis syndrome in an animal species (e.g., domestic cats) in which pathogenic amoeba colonize extraocular tissues causing disease that is clinically identical to those described in humans with amoeba corneal infection.

Amoeba, as used herein refers to a protozoan, preferably a pathogenic protozoan, isolated from the environment or from mammals (animals or human). Amoeba generally belong to the families acanthamoebidae and vahlkamfiidae. Acanthamoebidae family encompass the genus *Acanthamoeba* and members of this genus include amoeba species (spp.), such as but not limited to, *A. castellanii, A. commandoni, A. culbertsoni, A. divionensisi, A. echinulata, A. griffin, A. hatchetti, A. healyi, A. jacobsi, A. lenticulata, A. lugdunensis, A. mauritaniensis, A. palestinensis, A. pearcei, A. polyphaga, A. pustulosaj, A. quina, A. rhysodes, A. royreba, A. stevensoni, A. triangularis, A. tubiashi*. The term amoeba, as used herein, is also meant to include other disease causing amoebae, which may or may not belong to acanthamoebidae and vahlkamfiidae families, such as but not limited to, *Entamoeba histolytica, Naegleria, Balamuthia, Hartmannella*. Additionally, the term amoeba also includes species that play hosts to bacterial pathogens, such as, by protecting them from disinfectants and allowing their multiplication within amoebal cysts. Furthermore, the term amoeba is also meant to include an as yet identified amoeba species, which preferably is a causative agent for ocular complications in mammals.

The animal species, as used herein, belong to the felidae family of which the most familiar felid is the cat (i.e., domesticated cats).

Corneal symptom or a disease, as used herein, refers to conditions of injured cornea caused by amoebic infections and include symptoms or diseases, such as but not limited to, colonization of the extraocular tissues, conical epithelial irregularity, an epithelial ulcer, a stromal infiltrate, a stromal ulcer, a radial keratoneuritis, a keratomalacia, a limbititis, perineuritis, a corneal microcyst, a punctate keratopathy, a bullous keratopathy, a disciform stromal keratitis, a pseudodendritic keratitis, an anterior uveitis, a granulomatous stromal reaction, a stromal ring infiltrate formation, a conjunctivitis, a keratitis, a mucopurulent ocular discharge, an intermittent blepharospasm, a moderate conjunctivitis, an axial corneal edema, a multifocal linear anterior stromal leukocyte infiltration, a superficial corneal ulceration, a blepharitis, a scleritis, a cataract, a chorioretinitis, a corneal stromal abscess or a combination thereof.

The animal models created by the methods of the invention will enable screening of therapeutic agents useful for treating or preventing an ocular complication (e.g., keratitis). Accordingly, the present invention provides methods for identifying therapeutic agents for treating or preventing an ocular complication (e.g., keratitis). The methods comprise administering a candidate agent to an animal model made by the methods of the present invention, assessing at least one ocular complication (e.g., progress of keratitis) in the animal model as compared to a control animal model to which the candidate agent has not been administered. If at least one ocular complication (e.g., keratitis) is reduced in symptoms or delayed in onset, the candidate agent is an agent for treating or preventing the ocular complication (e.g., keratitis).

The term "treating" refers to any indicia of success in the treatment or amelioration or prevention of an ocular disease, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an eye examination. Accordingly, the term "treating" includes the administration of compounds or agents to prevent or delay, to alleviate, or to arrest or inhibit development of the symptoms or conditions associated with ocular disease. The term "therapeutic effect" refers to the reduction, elimination, or prevention of the disease, symptoms of the disease, or side effects of the disease in the subject.

In a non limiting example, the efficacy of a compound, referred to herein as compound X, to treat *Acanthamoeba* induced ocular complication (e.g., conjunctivitis or keratitis) can be screened as follows: Compound X, in a therapeutically effective amount, is applied either topically or systemically in appropriate buffers and excipients routinely used for ophthalmic application either (i) prior to *Acanthamoeba* inoculation (ii) with *Acanthamoeba* inoculation or (iii) after *Acanthamoeba* inoculation in a test animal but not in a control animal (i.e., an animal that is infected in a substantially similar manner with *Acanthamoeba* but untreated with compound X). The progression of the disease is then monitored by one or more parameters, such as but not limited to, development of corneal lesions and the rapidity of their regression, clinical ocular disease scores, frequency of amoeba detection by culture, frequency of amoeba detection by confocal microscopy, frequency of amoeba detection by histopathology, frequency of amoeba detection by immunohistochemistry, development and grading of histologic lesions. These parameters could be assessed periodically, such as, on an hourly, a daily, a weekly or a monthly basis, depending on the onset of an infection or the rapidness of the disease progression. Irrespective of the duration of application of the compound, the compound's efficacy will be defined by its ability to reduce the symptoms or ameliorate a particular ocular complication. For example, if in the control animal, which was not treated with compound X, symptoms, such as conjunctivitis or keratitis developed but not in the animal that was treated with the compound X, this would be a measure of the efficacy of compound X. Compound X identified by the method of the present invention can be utilized to treat a disease state associated with *Acanthamoeba*.

As an alternative to using a test animal and a control animal (i.e., animals divided into one or more groups), such studies could also be performed in a single animal. When performed in a single animal it is preferred that one eye of the animal serves as a test eye and the other eye as a control eye, wherein one or both eyes may be subjected to ophthalmic infection.

In another non limiting example, the efficacy of two different compounds, referred to herein as compound X and compound Y, to treat *Acanthamoeba* induced ocular complication (e.g., conjunctivitis or keratitis) can be screened as follows: Compounds X and Y may be independently or simultaneously, in therapeutically effective amounts, applied either topically or systemically in appropriate buffers and excipients routinely used for ophthalmic application either (i) prior to *Acanthamoeba* inoculation (ii) with *Acanthamoeba* inoculation or (iii) after *Acanthamoeba* inoculation in a test animal but not in a control animal (i.e. an animal that is infected in substantially similar manner with *Acanthamoeba* but untreated with compounds X and Y). The progression of the disease is then monitored by one or more parameters, such as but not limited to, development of corneal lesions and the rapidity of their regression, clinical ocular disease scores, frequency of amoeba detection by culture, frequency of amoeba detection by confocal microscopy, frequency of amoeba detection by histopathology, frequency of amoeba detection by immunohistochemistry, development and grading of histologic lesions. These parameters could be assessed periodically, such as, an hourly, a daily, a weekly or a monthly basis, depending on the onset of an infection or the rapidness of the disease progression. Irrespective of the duration of application of the compounds or the order of application of the compounds, (i.e., X preceding Y or Y preceding X, or simultaneously applying X and Y) the compounds' efficacy will be defined by their ability to reduce the symptoms or ameliorate a particular ocular complication. For example, if in the control animal, which was not treated with compounds X and Y, symptoms, such as conjunctivitis or keratitis developed but not in the animal that was treated with the compounds X and Y, this would be a measure of the combinational efficacy of the compound X and Y. The combinational use of compounds X and Y identified by the method of the present invention can be utilized to treat disease states associated with Acanthamoeba.

Examples of one or more candidate agents (e.g., X and/or Y, discussed above) that could be screened in the above examples include, but are not limited to, one or more of diamidines (e.g., propamidine isethionate, hexamidine, pentamidine), biguanides (e.g., polyhexamethylene biguanide, chlorhexidine, alexidine), imidazoles (e.g., clotrimazole, intraconazole, vitraconazole), antifungals (eg, caspofungin, natamycin), aminoglycosides (e.g., neomycin), macrolides (e.g., rokitamycin), antineoplastic agents (e.g., miltefosine), metronidazole, plant extracts (e.g., from Rubus chamaemorus, Pueraria lobata, Solidago virgaurea and Solidago graminifolia, Pterocaulon polystachyum, Allium sativum, Thymus sipyleus), N-chlorotaurine propolis, amidoamine myristamidopropyl dimethylamine or derivatives thereof or combinations thereof with other known or unknown compounds.

In another non-limiting example, a source suspected of being contaminated with Acanthamoeba spp., such as, a contact lens or a contact lens disinfectant, may be screened for the presence of Acanthamoeba spp. In this example, the efficacy of a contact lens or contact lens disinfectant to eliminate Acanthamoeba or prevent its transmission to the eye could be evaluated by experimentally contaminating the contact lens and then placing the lens on the cat eye and monitoring for development of Acanthamoeba keratitis. In the case of the contact lens disinfectant, the lens would be contaminated with the amoeba and then disinfected with the contact lens disinfectant prior to placing the lens on the cat. Once brought in contact with the eye, progression of one or more Acanthamoeba induced disease or symptom is monitored by one or more parameters, such as but not limited to, development of corneal lesions and the rapidity of their regression, clinical ocular disease scores, frequency of amoeba detection by culture, frequency of amoeba detection by confocal microscopy, frequency of amoeba detection by histopathology, frequency of amoeba detection by immunohistochemistry, development and grading of histologic lesions. These parameters could be assessed periodically, such as, on an hourly, a daily, a weekly or a monthly basis, depending on the onset of an infection or the rapidness of the disease progression. Development of symptoms, such as conjunctivitis or keratitis, typically associated with Acanthamoeba species, is indicative that the contact lens is associated with Acanthamoeba. It is possible to include a control animal in such a study, wherein such control animal has been subjected to sham treatment. One of skill in the art will understand that other contaminating sources for Acanthamoeba can be tested in a manner as described above.

Ophthalmic preparation characteristics and routes of administration are known to one of skill in the art and are disclosed, for example, at least in chapter 43 (Authors: Lang, J. C. et al.,) of Remington: the science and practice of pharmacy $21^{st}$ edition, Lippincot, Williams and Wilkins publishers; Bartlett J D, Jaanus S D., (Editors) Ocular Pharmacology 5th edition, 2007, Butterworth-Heinemann Publisher; Sunqupta K K, Mukherji R. Essentials of Ocular Pharmacology and Therapeutics, 2007, Anshan Publisher; Mauger T F, Craig E L., Havener's Ocular Pharmacology $6^{th}$ edition, 1994, Mosby Publisher. The entire contents of which are incorporated herein by reference.

While topical, intraocular, intracorneal, intracameral, and systemic routes (e.g., intravenous routes) are preferred routes for administration for the compounds or agents for screening, other routes include, but are not limited to, parenteral (e.g., intravenous), intramuscular, intradermal, intraperitoneal, subcutaneous, transdermal, extracorporeal or the like, in any combination and in any order.

Treatments described herein can be administered and monitored by an ordinarily skilled clinician. Administration routes, dosages and specific measures of efficacy can be selected by the administering clinician, and will depend upon factors such as the specific Acanthamoeba induced symptom or disease involved, severity of that disease, age, as well as other factors, such as other medical problems faced by the patient concurrently.

The candidate agents used in the invention may be pharmacologic agents already known in the art or may be agents previously unknown to have any pharmacological activity. The agents may be naturally arising or designed in the laboratory. They may be isolated from microorganisms, animals, or plants, or may be produced recombinantly, or synthesized by chemical methods known in the art. They may be small molecules, nucleic acids, proteins, peptides or peptidomimetics. In certain embodiments, candidate agents are small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof. In certain embodiments, efficacy of various other treatment modalities e.g., keratoplasty, amniotic membrane transplantation, riboflavin and ultraviolet light therapy, phototherapeutic keratectomy, photodynamic therapy, immunization, either alone or in combination with other agents or compounds disclosed herein could be evaluated.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. In certain embodiments, the candidate agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. (Lam, Anticancer Drug Des. 12: 145, 1997).

Examples of methods for the synthesis of molecular libraries can be found in the art, for example in: DeWitt et al. Proc. Natl. Acad. Sci. U.S.A. 90: 6909, 1993; Erb et al. Proc. Natl. Acad. Sci. U.S.A. 91:11422, 1994; Zuckermann et al., J. Med. Chem. 37: 2678, 1994; Cho et al., Science 261: 1303, 1993; Carrell et al., Angew. Chem. Int. Ed. Engl. 33: 2059, 1994; Carell et al., Angew. Chem. Int. Ed, Engl. 33: 2061, 1994; Kuruvilla et al., Nature 416: 653-657, 2002; and in Gallop et al., J. Med. Chem. 37: 1233, 1994. All publications are incorporated by reference in their entirety.

In certain further embodiments, known pharmacological agents may be subjected to directed or random chemical modifications, such as acylation, alkylation, esterification, amidification, etc. to produce structural analogs. The methods discussed above for identifying therapeutic agents for treating a ocular complication can also be used to validate lead compounds/agents generated from in vitro studies.

Amoebae are distributed worldwide and have been isolated from soil, dust, air, natural and treated water, seawater, swimming pools, sewage, sediments, air-conditioning units, domestic tap water, drinking water treatment plants, bottled water, dental treatment units, hospitals and dialysis units, eyewash stations, and contact lenses and lens cases and as contaminants in bacterial, yeast, and mammalian cell cultures. *Acanthamoeba* spp. also have been isolated from vegetation, from animals including fish, amphibia, reptiles, and mammals from the nasal mucosa and throats of apparently healthy humans and have been found to be causative agents for various diseases. As an example, there have been several human outbreaks of *Acanthamoeba* keratitis in the last few years associated with contact lens solutions that failed to disinfect *Acanthamoeba* or promoted organism encystment. Therefore, in one embodiment, the animal model could easily be used to screen such sources, (e.g., disinfectant solutions) for their ability to limit *Acanthamoeba* spp, specifically those that are involved in ocular complications, for example transmission to the cornea. The animal model could also be used to screen disinfection efficacy (e.g., of a contact lens solution) against *Acanthamoeba*.

As shown in more detail in the experimental sections, Applicants have demonstrated that the ocularly infected cats with pathogen amoeba show classic symptoms of *Acanthamoeba* induced ocular complications (e.g., keratitis progression) that are similar to those seen in human patients. Accordingly, the present invention further provides methods for validating lead compounds/agents generated from in vitro studies. In the methods, an infected cat is administered a lead compound for treating ocular complications (e.g., keratitis) at various stages of the disease. At appropriate time points, the cat is examined for one or more ocular complications (e.g., inhibition in progression of keratitis). If the cat shows reduced symptoms of an ocular complication (e.g., keratitis) compared to a control cat that did not receive the lead compound, the lead compound is a validated compound for treating an ocular complication (e.g., keratitis).

To practice one or more aspects of the present invention one of skill in the art may employ, unless otherwise indicated, conventional techniques of cell biology, cell culture, molecular biology, transgenic biology, microbiology, recombinant DNA, and immunology, Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (Glover ed., 1985); Oligonucleotide Synthesis (Gait ed., 1984); Mullis et al. U.S. Pat. No. 4,683,195; Nucleic Acid Hybridization (Hames & Higgins eds., 1984); Transcription And Translation (Hames & Higgins eds., 1984); Culture Of Animal Cells (R. I. Freshney, Alan R. Liss, Inc., 1987); Immobilized Cells And Enzymes (IRL Press, 1986); Perbal, A Practical Guide To Molecular Cloning (1984); the treatise, Methods In Enzymology (Academic Press, Inc., N.Y.); Gene Transfer Vectors For Mammalian Cells (Miller and Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (Weir and Blackwell, eds., 1986); Clinical Microbiology Reviews, April 2003, p. 273-307, Vol. 16, No. 2. All publications are incorporated by reference in their entirety.

The invention now being generally described, it will be more readily understood by reference to the following examples, which are included merely for purposes of illustration of certain embodiments and embodiments of the present invention, and are not intended to limit the invention.

In one embodiment of this study cats with ulcerative and non-ulcerative keratitis are disclosed to determine the frequency of amoeba detection in cats with keratitis, risk factors for the presence of amoeba, and the relative utility of several amoeba detection methods in cats. Four independent methods of amoeba detection were employed. Corneal scrapings collected from cats presented with keratitis were analyzed by routine amoeba culture using enteric gram-negative bacteria supplemented agar, cytological evaluation with Wright and periodic-acid-Schiff (PAS) stains, and a multiplex PCR assay for several genera of amoebae with demonstrated corneal pathogenicity in humans. Cats were examined with in vivo corneal confocal microscopy to determine the presence or absence of amoeba within corneal tissue. Aerobic bacterial culture and feline herpesvirus-1 PCR were performed concurrently for each corneal sample to exclude other common etiologies of feline corneal disease in cats with positive amoeba diagnostic assays to determine if co-infections were present. For statistical comparison and to determine if *Acanthamoeba* is a component of the normal extraocular microflora of cats, ocular swab specimens can be collected from cats without clinically detectable extraocular disease for amoeba culture, cytology, and amoeba PCR. Historical and clinical data for cats with keratitis is statistically compared between cats with positive amoeba assays and with negative assays, and the sensitivity and specificity of each amoeba detection method is determined.

Figure 2:
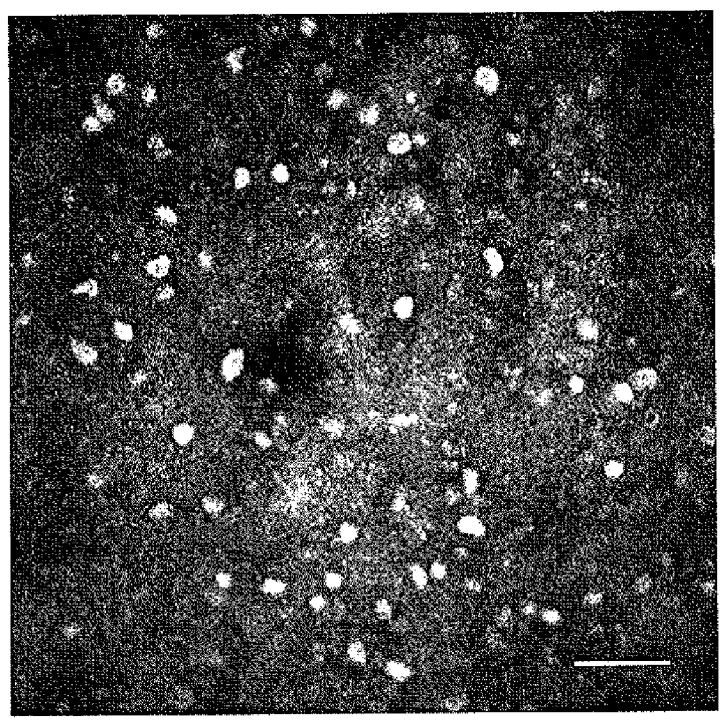
FIG. 2 shows in vivo corneal confocal photomicrograph of a cat with naturally-acquired *Acanthamoeba* keratitis. Numerous high contrast double-walled amoeba cysts and trophozoites are present in the epithelium and superficial stroma (Bar=50 µm).

The following disclosure provides for the first identification of an animal with a spontaneously occurring *Acanthamoeba* keratitis syndrome which is predictive of a similar syndrome in humans. All together 120 cats were enrolled in the study, including 60 with various forms of keratitis and 60 without clinically apparent ocular disease. *Acanthamoeba* ocular infection was confirmed in 2 cats. One of these cats was presented with ulcerative keratitis and one with conjunctivitis. The cat with *Acanthamoeba* keratitis was presented 2 weeks post-corneal trauma with superficial ulcerative keratitis associated with diffuse corneal epithelial and subepithelial infiltrates, mild diffuse corneal edema, anterior stromal vascularization, and anterior uveitis (FIG. 1). The cat with *Acanthamoeba* conjunctivitis was clinically normal, but suppurative conjunctivitis was detected by cytology. In both cats, viable *Acanthamoeba* spp. were isolated on culture. In the cat with keratitis, *Acanthamoeba* DNA was detected by PCR, and amoeba cysts and trophozoites were observed by cytology and in vivo corneal confocal microscopy (FIG. 2). Feline herpesvirus-1 PCR assays and bacterial cultures were negative. In the cat with keratitis, the ocular lesions progressed over the subsequent 4 weeks to non-ulcerative stromal keratitis associated with a dense paracentral corneal stroma ring infiltrate, a classic late-stage *Acanthamoeba* keratitis lesions in humans. These findings demonstrate the cat is an ideal experimental model for human *Acanthamoeba* keratitis. This animal model has the unique and important benefit of being developed in a species with a known, naturally-occurring disease state similar to humans.

One of the requirements for *Acanthamoeba* to establish corneal infection is the ability of the parasite to bind to, and subsequently invade, the host's corneal surface. Previous in vitro and in vivo studies have determined that *Acanthamoeba* displays rigid host specificity at the level of the corneal surface. In vitro studies investigating the ability of *Acanthamoeba* to bind to the human, pig, hamster, mouse, rat, cotton rat, horse, guinea pig, cow, chicken, dog, and rabbit cornea have been performed. Of these host species corneas, *Acanthamoeba* was only capable of binding in vitro to the human, hamster, and pig corneas. Subsequent studies have determined that the ability to bind to the corneal surface in vitro correlates with in vivo susceptibility to *Acanthamoeba* keratitis. Numerous studies have demonstrated that *Acanthamoeba* keratitis cannot be experimentally induced in host species where the parasite is unable to bind to the cornea in vitro and naturally-acquired infection has not been reported in these animal species.

A determination was made of the susceptibility of the intact and traumatized feline cornea to in vitro *Acanthamoeba* binding relative to a host species with established susceptibility to *Acanthamoeba* binding (i.e., pig) and a host species with established resistance to *Acanthamoeba* binding (i.e., dog). Feline, porcine, and canine fresh corneas were collected and cut into 6.0 mm diameter full-thickness sections. Corneal epithelium was confirmed intact by fluorescein staining or lightly scarified with a 25 gauge needle in a grid pattern to simulate corneal trauma. *Acanthamoeba castellanii* (ATCC #30868) was cultivated axenically to a concentration of $3\times10^6$ amoebae/mL (90% trophozoites and 10% cysts). Corneal sections were incubated with the parasite suspension or parasite-free medium for 18 hours at 35° C. Corneal sections were rinsed, fixed, and processed for histopathology with hematoxylin & eosin and periodic-acid-Schiff stains, immunohistochemistry using rat anti-*Acanthamoeba castellanii* polyclonal antibody, and electron microscopy.

Figure 3:
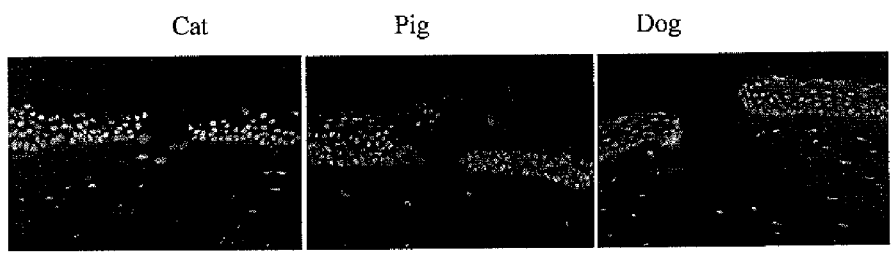
FIG. 3 shows *Acanthamoeba* in cat, pig, and dog traumatized corneal tissue sections visualized using an immunofluorescence method with Texas Red and Dapi counterstain. Numerous organisms are present in regions of epithelial damage in cat and pig corneal sections. Traumatized canine corneal sections are free of adherent amoebae.
Figure 4:
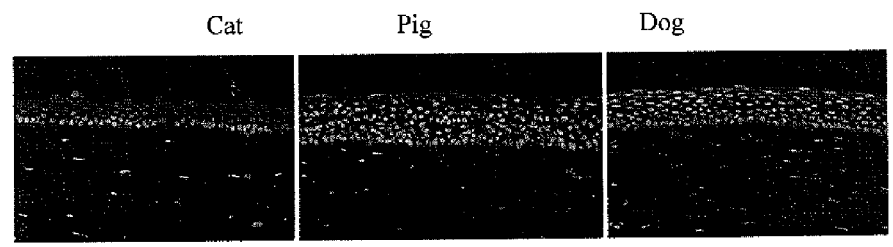
FIG. 4 shows *Acanthamoeba* in cat, pig, and dog intact corneal tissue sections visualized using an immunofluorescence method with Texas Red and Dapi counterstain. In cat and pig corneal sections, amoebae are detected at all levels of the corneal epithelium and within the anterior stroma. Intact canine corneal sections are fee of adherent amoebae.

Numerous amoebae were bound to feline and porcine corneas incubated with the parasite. In both intact and traumatized corneas, amoebae were detected at all levels of the corneal epithelium and within the anterior stroma (FIGS. 3 and 4). In traumatized corneal sections, clumps of numerous organisms were frequently present in regions of epithelial damage. Corneal architecture was well-preserved in sections incubated with parasite-free medium; however, epithelial cell sloughing and epithelial detachment from the stroma were observed in corneas incubated with amoebae. Intact and traumatized canine corneas were free of adherent amoebae and corneal architecture was indistinguishable between sections incubated with the parasite suspension and parasite-free medium (FIGS. 3 and 4).

This finding demonstrates that the feline cornea is highly susceptible to in vitro binding and invasion by *Acanthamoeba* and that this corneal binding does not require a prior epithelial defect. This characteristic likely contributes to the domestic cat's vulnerability to naturally-acquired *Acanthamoeba* keratitis and supports the use of the cat as a model of human *Acanthamoeba* keratitis.

Figure 5:
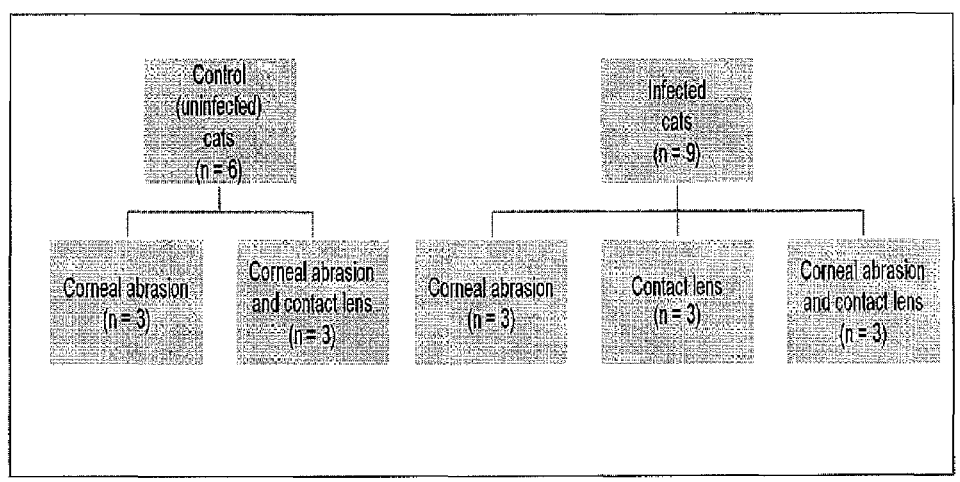
FIG. 5 shows study groups.

Animals—Fifteen 8-month old, specific-pathogen free, domestic shorthair cats were used in this study. Purpose-bred laboratory cats were acquired from a local vendor (Liberty Research, Inc., NY) and examined clinically and by in vivo corneal confocal microscopy prior to the study to exclude animals with preexisting ocular abnormalities. Following a 2 week acclimation period, cats were randomly allocated to one of 5 study groups (FIG. 5), each consisting of 3 cats: 1) topical *Acanthamoeba* inoculation following corneal abrasion, 2) contact lens *Acanthamoeba* inoculation without corneal abrasion 3) contact lens *Acanthamoeba* inoculation following corneal abrasion, 4) corneal abrasion only, and 5) contact lens and corneal abrasion only. Groups 1, 2, and 3 comprised the infection groups and groups 4 and 5 the control groups. These general methods of experimentally inducing *Acanthamoeba* keratitis have been previously reported in other animal species.

*Acanthamoeba* isolate—Axenic cultures of *Acanthamoeba castellanii* (ATCC #50514, #30868, Rockville Md. or similar strains), originally isolated from a human cornea and used in previous experimental animal studies, were grown in peptone-yeast-glucose medium known to one skilled in the art.

Contact lens preparation—Hydrophilic soft contact lenses designed for cats (Acrivet Inc, Hennigsdorf, Germany) and fitted to the corneal diameter of each individual study cat, were incubated for 24 hours at 35° C. with *Acanthamoeba castellanii* in 2.0 mL of peptone-yeast-glucose medium (amoeba concentration $3\times10^6$ organisms/mL) in sterile culture cluster wells. Similarly, contact lenses for the control groups were incubated for 24 hours at 35° C. in 2.0 mL of sterile peptone-yeast-glucose medium that was devoid of amoebae.

Corneal inoculations—All experimental procedures were performed on the right eye only of each cat. Cats were sedated with intravenous ketamine (3.0 mg/kg) and valium (0.3 mg/kg). Topical ophthalmic proparacaine is applied to the surface of the right eye. In groups 1 and 3, a 22 gauge needle is used to superficially abrade the central corneal epithelium in a cross-hatch pattern with two rows of abrasions oriented perpendicular to each other (a total of 10 linear parallel abrasions will be made in each plane). Immediately following corneal abrasions, the cornea is irrigated with 0.2 mL of a $3\times10^6$ amoeba/mL solution from a tuberculin syringe (group 1) or a parasite-laden contact lens were applied (group 3). In group 2, a parasite-laden contact lens was applied without corneal abrasion. Control groups were handled in a similar fashion; however, the cornea was irrigated with 0.2 mL of peptone-yeast-glucose medium (group 4) or a sterile contact lens (incubated in sterile peptone-yeast-glucose medium) was applied (group 5). All cats were fitted with an Elizabethan collar immediately following infection or sham inoculation to prevent dislodgement of contact lenses and self-trauma. All cats received subcutaneous buprenorphine (0.1 mg/kg, q12h) for a minimum of 72 hours post-inoculation for analgesia. Contact lenses were manually removed on study day 7 from all cats and evaluated by amoeba culture.

Figure 6:
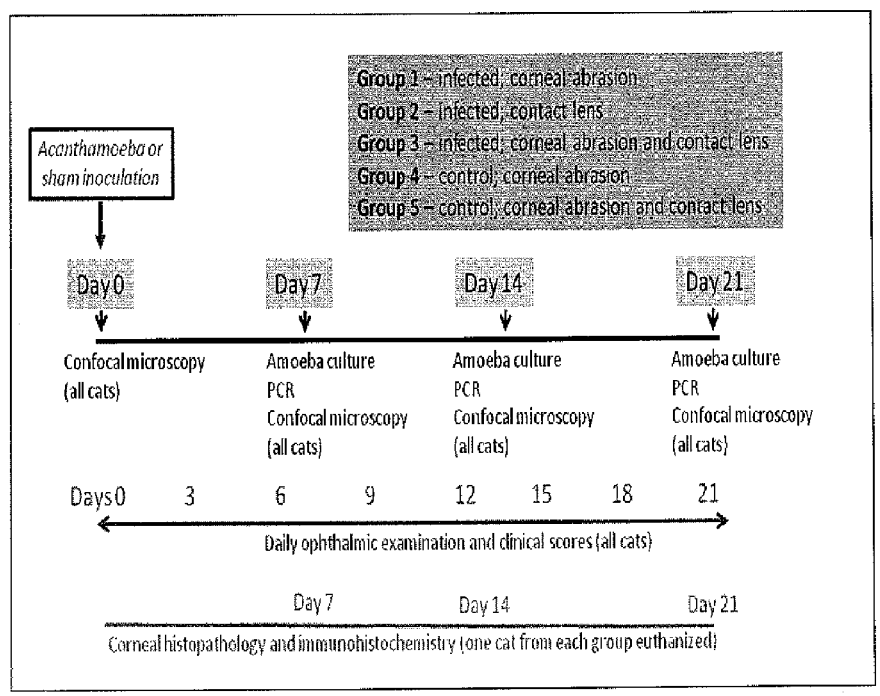
FIG. 6 shows study design with sample and examination schedule.

Examination and sample collection—Ophthalmologic examinations of both eyes with slit-lamp biomicroscopy (Kowa S L-15; Kowa Co., Ltd., Japan) and fluorescein staining were performed daily during the study and representative digital photographs of the eyes were taken (FIG. 6). A previously reported clinical scoring system for experimental *Acanthamoeba* keratitis was used and daily clinical scores calculated. The minimum daily score possible with this system is 0 and the maximum is 16.

TABLE 1 clinical scoring system for experimental *Acanthamoeba* keratitis

| Epithelial Defects | Stromal Edema | Vascularity | Stromal Opacity |
|---|---|---|---|
| 0 = no defects | 0 = no edema | 0 = no vessels | 0 = clear stroma |
| 1 = defects <25% surface area | 1 = edema <25% surface area | 1 = vessels on <25% corneal circumference | 1 = opacity <25% of corneal area, pupil easily visible |
| 2 = defect 25-50% of surface area | 2 = edema 25-50% of surface area | 2 = vessels on 25-50% corneal circumference | 2 = opacity 25-50%, of corneal area, pupil difficult to visualize |
| 3 = defect 50-75% surface area | 3 = edema 50-75% surface area | 3 = vessels on 50-75% corneal circumference | 3 = opacity 50-75% of corneal area, pupil not visible |
| 4 = defect >75% surface area | 4 = edema >75% surface area | 4 = vessels on >75% corneal circumference | 4 = opacity >75% of corneal area, pupil and iris not visible |

All cats were sedated with intravenous ketamine (3.0 mg/kg) and valium (0.3 mg/kg) at 7, 14, and 21 days post-inoculation for sample collection and in vivo corneal confocal microscopy as described later (FIG. 6). Following the application of topical proparacaine, corneal samples for culture and PCR were collected by gently scraping the central cornea with a Kimura spatula. Corneal scrapings were directly transferred to sterile polyester-tipped swabs and placed in sterile containers. Samples for PCR were frozen at −80° C. until analysis and samples for amoeba culture were processed immediately.

Following in vivo corneal confocal microscopy and sample collections, one randomly selected cat from each study group was euthanized by pentobarbital overdose (120 mg/kg IV) on days 7, 14, and 21 days post-inoculation. Globes were enucleated post-mortem. Half of each cornea was aseptically dissected from the globe down the central meridian, and divided into equal portions for amoeba culture and aerobic bacterial culture. Culture samples were immediately processed. The remainder of the cornea and the globe was fixed in 5% neutral buffered formalin for histopathology and immunohistochemistry. Following postmortem enucleation, euthanized cats were submitted to the New York State Animal Health Diagnostic Laboratory for complete necropsy to exclude the development of extraocular *Acanthamoeba* disease.

In vivo corneal confocal microscopy—Under topical anesthesia and sedation, in vivo corneal confocal microscopy was performed using a Heidelberg Retinal Tomograph II and the Rostock Corneal Module (Heidelberg Engineering, Inc., CA). A methylcellulose solution (Genteal tear gel) was applied to the corneal surface and a single-use; disposable, sterile PMMA lens cap (Tomocap™; Heidelberg Engineering, Inc., CA) placed on the end of the microscope objective was positioned in the gel adjacent to the corneal surface. Full-thickness multipoint imaging of the cornea was performed using a combination of automated and manual image acquisition modes. The image acquisition time of this instrument is 0.024 seconds/image with 2 micron resolution and a 400×400 micron field of view. Images were digitally stored and evaluated for pathology, including the presence of amoeba cysts and trophozoites, at the conclusion of the imaging study. With confocal microscopy, amoebae were readily detectable as 10-35 micron diameter structures. Amoeba cysts appear as high-contrast, double-walled, round bodies and trophozoites appear as high-contrast, double-walled, ovoid or irregular forms.

Amoeba culture—Corneal samples were cultured onto non-nutrient agar inoculated with *Escherichia coli* strain JM109 to determine if viable amoebae were present. Samples were divided and incubated at room temperature, 37° C., and 44° C. Cultures were examined daily for 14 days with inverted and compound microscopes for growth. Taxonomic identifications were made based upon microscopic morphology of cysts and trophozoites.

Feline herpesvirus-1 SYBR green real-time PCR assay—Assays were performed in a real-time PCR detection system (Applied BioSystems, Foster City, Calif., USA) using a Platinum SYBR Green qPCR SuperMix-UDG kit (Invitrogen, Carlsbad, Calif., USA). The thermocycling conditions included preincubation for 2 min at 50° C. to prevent the amplification of carryover PCR products, denaturation for 2 min at 95° C., 40 cycles of denaturation at 95° C. for 15 s, and annealing and extension at 60° C. for 1 min. Previously described primers were employed as follows: FHV TK and TK rev for the FHV-1 thymidine kinase (TK) gene. The fluorescence intensity of SYBR green was measured and a melting curve analysis was performed at the end of each run.

Aerobic bacterial culture—Standard microbiological culturing methods were employed. Direct cultures on solid media (trypticase soy agar with 5% sheep blood, chocolate agar, Levine EMB, and Columbia CAN) were performed for each sample. Direct cultures were incubated at 35° C. in 6% $CO_2$ and read at 24 and 48 hours. All microorganism identifications were performed with an automated system (Sensititre®, Trek Diagnostic Systems Inc., Cleveland, Ohio).

Histopathology and immunohistochemistry—Three micron sections of formalin fixed corneas were cut and stained with hematoxylin and eosin and PAS for standard histopathology. Four micron thick sections of formalin-fixed/paraffin-embedded globes were used for immunohistochemical analysis. After deparaffinization in xylene and rehydration in graded ethanol, antigen retrieval was performed by heating sections in citrate buffer (0.01 mol/L, pH 6.0) for 2×10 minutes. Endogenous peroxidase activity was quenched with 3% hydrogen peroxide in methanol for 10 minutes. Nonspecific staining was blocked with a mixture of 10% goat serum and 2× casein for 30 minutes at room temperature. The primary antibody was a rat anti-*Acanthamoeba castellanii* polyclonal antibody from Antibody Systems Inc (1:500 diluted in PBS containing 1× casein) and was added for 1.5 hr at 37° C. The second antibody was a biotinylated goat anti-rabbit IgG (Vector Laboratories) used at 1:200 dilution in PBS and added for 30 min at room temperature. In the case of enzymatic-based detection, Avidin-biotin-peroxidase complex method was followed. AEC or Nova Red (Invitrogen) was used as chromogen, and the sections were lightly counterstained with hematoxylin. In case of fluorescent detection, streptavidin-Texas Red (Molecular Probe) at 1:200 in PBS was used to visualize antibody-specific binding and the sections were counterstained with Dapi (Vector Laboratories). PBST (0.05% Tween 20) was used for washing throughout the procedure. Rat serum at the same final protein concentration was used as a negative control. Immunohistochemical results were examined and photographed using Olympus AX 70 compound microscope.

Data analysis—The frequency of clinical ocular lesions, the daily clinical ocular disease scores, and frequency of positive in vivo corneal confocal microscopic examinations, amoeba cultures, and immunohistochemical corneal evaluations was compared between the infection and control groups using descriptive statistics, Fischer's exact test, and the Student's t-test for each examination and sampling day. A P≤0.05 was considered significant for all comparisons. Additionally, detailed descriptions of the clinical, histopathologic, in vivo confocal microscopic, and immunohistochemical ocular lesions were collected.

Quantitative polymerase chain reaction—It is possible to perform a real-time PCR assay for *Acanthamoeba* detection to quantitate the number of amoeba present. For this procedure, amoeba DNA can be extracted by using the DNeasy Tissue kit (Qiagen) according to the manufacturer's instructions. The DNA real-time amplification reaction is performed on an AB 7500 sequence detection system (Applied Biosystems, Foster City, Calif.). Two genera-specific primers selected from the literature is used targeting *Acanthamoeba* 16S rRNA f and mitochondrial small subunit rRNA. Each reaction mix typically will contain a total of 25 including 12.5 µl 2× Power SYBR mix (Applied Biosystems), each primer at a concentration of 0.2 µM, 5 µl template DNA and DNAse-free water. The thermal cycling conditions include 1 cycle of decontamination at 50° C. for 2 min, 1 cycle of activation at 95° C. for 10 min, 40 cycles of denaturation at 95° C. for 15 seconds, annealing and extension at 60° C. for 1 min. The fluorescence intensity of SYBR green is measured automatically during the annealing step. At the end of each PCR run, a melting-curve analysis is performed to determine the specificity of each positive signal. Experiments are performed with undiluted and 10-fold diluted template DNA in duplicate. For quantification, when needed, a cell based calibration curve is constructed by preparing 10-fold serial dilutions of known DNA templates, Real time PCR is a routinely applied laboratory technique and one of skill in the art will know how to modify this protocol for the detection of the *Acanthamoeba* spp.

Description of Experimental Feline *Acanthamoeba* Keratitis Model Results

Figure 7:
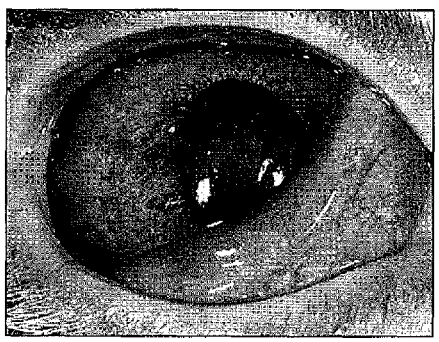
FIG. 7 shows clinical photographs of 2 cats with experimental *Acanthamoeba* keratitis. Epithelial and anterior stromal inflammatory infiltrates are associated with corneal edema and conjunctivitis.
Figure 7:

Clinical Findings—The clinical manifestations varied between groups. All cats in group 1 developed conjunctivitis and keratitis (FIG. 7). Mucopurulent ocular discharge, intermittent blepharospasm, moderate conjunctivitis, axial conical edema, multifocal linear anterior stromal leukocyte infiltrates, and geographic regions of superficial corneal ulceration were detected on study day 2. Initially corneal stromal infiltrates corresponded roughly to the linear conical abrasions made during inoculation, but extension of the infiltrates into the adjacent stroma beyond these abrasions occurred by study day 4 in all cats. The cornea was fluorescein negative by study day 8 in all cats. Axial corneal edema and multifocal anterior stromal leukocyte infiltrates persisted until study conclusion in all cats.

One cat from group 2 developed conjunctivitis and keratitis (FIG. 7). On study day 2, moderate diffuse axial epithelial leukocyte infiltrates were visible under the contact lens. Intermittent blepharospasm, mucopurulent discharge, and diffuse mild corneal edema were present on study day 3. These lesions progressed over the next 5 days to severe blepharitis, severe conjunctivitis marked and diffuse epithelial and subepithelial leukocyte infiltrates, and mild anterior uveitis (i.e., trace aqueous flare and miosis). A superficial corneal ulcer was detected on study day 7 after contact lens removal. Progressive 360° anterior stromal vascularization began on study day 7. The stroma in the region of ulceration developed a brown discoloration consistent with feline corneal sequestrum on study day 10. Diffuse, severe leukocyte infiltrates, conical ulceration, corneal edema, conjunctivitis, and anterior uveitis persisted until study day 14 when the cat was euthanized. The other 2 cats from group 2 did not develop detectable inflammatory ocular disease during the study.

All cats from group 3 developed conjunctivitis and keratitis (FIG. 7). Ocular lesions in this group followed a more fulminant course than the other two infection groups. In all cats, severe blepharitis, mucopurulent ocular discharge, blepharospasm, severe conjunctivitis, diffuse corneal edema, and diffuse corneal epithelial and subepithelial leukocyte infiltrates were present on study day 2. Leukocyte infiltrates consolidated into multifocal anterior and midstromal abscesses in all cats over the following 5 days and persisted until study conclusion. Geographic corneal ulcerations were detected between study days 7 and 18 in two cats. Mild anterior uveitis was variably present and progressive 360° anterior stromal vascularization began on study day 7.

Figure 8:
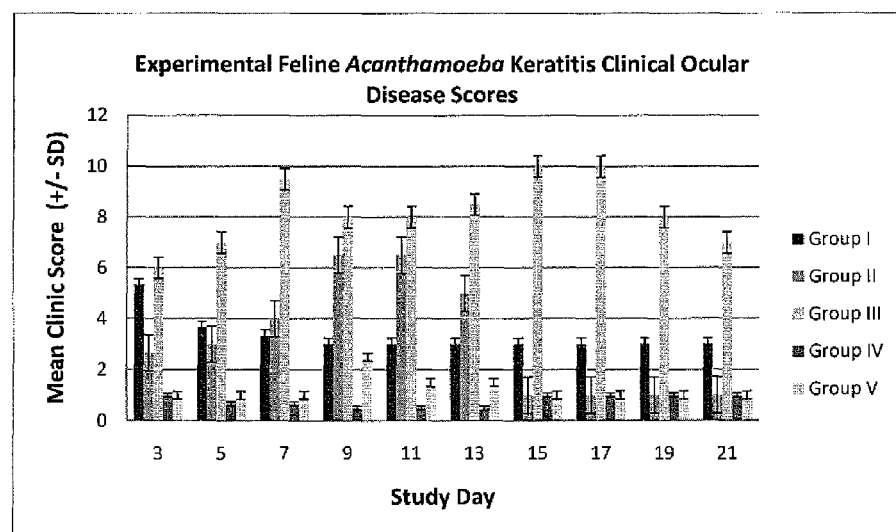
FIG. 8 shows daily mean clinical ocular disease scores for cats with experimental *Acanthamoeba* keratitis (groups I, II, and III) and control cats (groups IV and V).

No cats from groups 4 and 5 developed conjunctivitis or keratitis. The corneal abrasions had healed by study day 2 and 7 in group 4 and 5 respectively. Faint, semi-transparent, linear subepithelial opacities with sharp margins were visible by biomicroscopy in all cats corresponding with the regions of linear corneal abrasion made during sham inoculation. These linear opacities persisted until study conclusion in most cats, but progressively became more transparent. Blepharospasm, ocular discharge, and uveitis were not observed in any cat from the control groups. The frequency of keratitis was significantly (P=0.007) higher in the infection group (7 or 9 cats) than the control group (0 of 6 cats). Mean clinical ocular scores were significantly higher for the infection groups than the control groups on several of the selected comparison days as illustrated by the following examples (FIG. 8):

day 3: infection group mean score: 4.4 (+/−2.13 SD); control group mean score: 1.0 (+/−0.0 SD); P=0.002 day 5: infection group mean score: 4.2 (+/−2.39 SD); control group mean score: 0.86 (+/−0.38 SD); P=0.003 day 7: infection group mean score: 5.0 (+/−3.74 SD); control group mean score: 0.83 (+/−0.41 SD); P=0.02 day 9: infection group mean score: 5.5 (+/−3.89 SD); control group mean score: 1.0 (+/−0.82 SD); P=0.05

Figure 9:
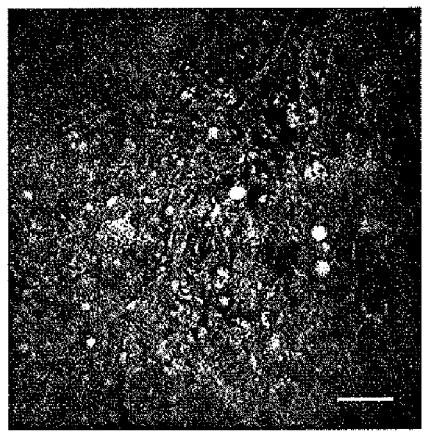
FIG. 9 shows in vivo confocal photomicrograph of amoebae within the basal epithelium of an experimentally infected cat (Bar=50 µm).
Figure 10:
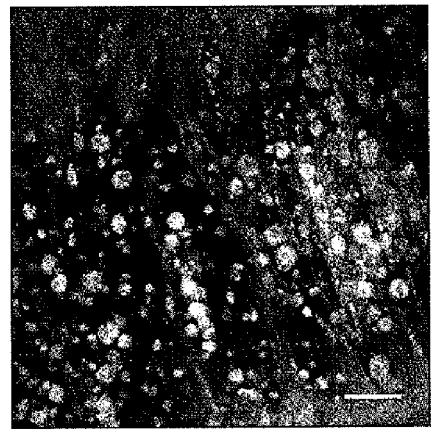
FIG. 10 shows in vivo confocal photomicrograph of amoebae within the anterior stroma of an experimentally infected cat (Bar=50 µm).

In vivo Confocal Microscopy—Structures consistent with amoeba cysts and trophozoites were detected on all examination days in the corneas of all cats from infection groups 1 and 3, and the single cat from infection group 2 that developed clinical keratitis (FIGS. 9 and 10). Numerous 10-35 micron diameter, high-contrast, double-walled, round and ovoid structures were detected within the basal epithelium and anterior stroma. These structures were associated with moderate to marked epithelial and stromal inflammatory infiltrates. Similar structures were not observed in corneas of cats from control groups 4 and 5, or 2 cats from infection group 2 that did not develop clinical ocular disease. The frequency of amoeba detection on one or more examination days by confocal microscopy was significantly (P=0.007) higher in the infection groups (7 of 9 cats) than the control groups (0 of 6 cats).

Figure 11:
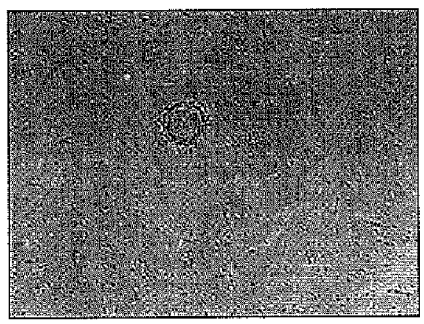
FIG. 11 shows *Acanthamoeba* cyst and trophozoites isolated from cats with experimental *Acanthamoeba* keratitis (original magnification 400×).
Figure 11:
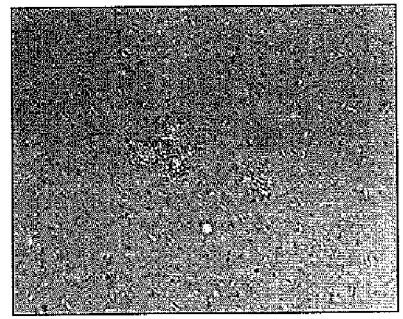

Acanthamoeba Culture—Viable Acanthamoeba were isolated from 9 samples of cats in study groups 1, 2, and 3 (FIG. 11). Six of 9 cats comprising the infection groups had at least one positive culture as describe in the culture results table. All contact lenses were culture negative. All amoeba cultures were negative for cats from the control groups 4 and 5. The frequency of positive amoeba cultures was significantly (P=0.004) higher in the infection groups (9 or 18 samples) than the control groups (0 of 12 samples).

| Study Group | Acanthamoeba Culture Result | | | |
|---|---|---|---|---|
| | Study day 7 | Study day 14 | Study day 21 | Total positive |
| Group 1 (infected, corneal abrasion) | 1 of 3 positive | 1 of 2 positive | 1 of 1 positive | 3 (50%) |
| Group 2 (infected, contact lens) | 0 of 3 positive | 0 of 2 positive | 0 of 1 positive | 0 (0%) |
| Group 3 (infected, corneal abrasion + contact lens) | 3 of 3 positive | 2 of 2 positive | 1 of 1 positive | 6 (100%) |
| Group 4 (control, corneal abrasion) | 0 of 3 positive | 0 of 2 positive | 0 of 1 positive | 0 (0%) |
| Group 5 (control, corneal abrasion + contact lens) | 0 of 3 positive | 0 of 2 positive | 0 of 1 positive | 0 (0%) |

Figure 12:
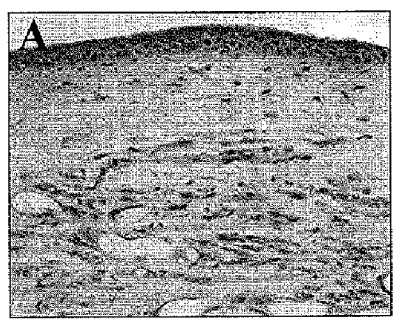
FIG. 12 shows photomicrographs of 2 cats with experimental *Acanthamoeba* keratitis. The corneal stroma is edematous, regionally infiltrated with leukocytes, and corneal vessels are present. Occasional *Acanthamoeba* are detected in the anterior and mid-stroma (original magnification: A: 200×; B: 400×).
Figure 12:

Histopathology and Immunohistochemistry—Histopathologic findings were similar in all cats from infection groups 1 and 3, and the single cat from infection group 2 that developed clinical keratitis (FIG. 12). Leukocyte infiltrates were present in the central cornea and characterized by predominantly neutrophils with fewer mononuclear cells. Inflammatory infiltrates were present at all levels of the corneal stroma, but were most marked in the anterior and midstroma. The corneal epithelium was intact in most samples, but was focally absent in the cats with ulcerative keratitis clinically present at the time of euthanasia. Edema, spindle-shaped cells, and blood vessels were variably present in the anterior and midstroma. Acanthamoeba trophozoites and cysts were most numerous in the in anterior and midstroma. Corneas from cats in control groups 4 and 5, and the 2 cats from infection group 2 that did not develop clinical ocular disease, were histopathologically unremarkable.

Figure 13:
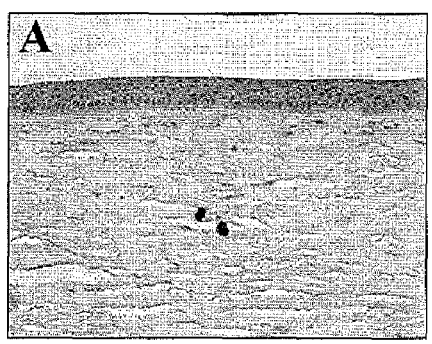
FIG. 13 shows photomicrographs of 2 cats with experimental *Acanthamoeba* keratitis. Positive immunohistochemical staining for *Acanthamoeba* is detected in the anterior stroma (original magnification: A: 200×; B: 400×).
Figure 13:
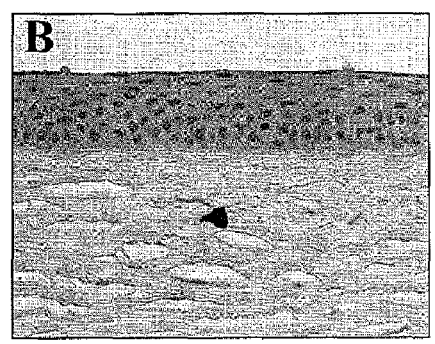

Positive immunohistochemical staining for Acanthamoeba was detected in the corneal epithelium or stroma of all cats from infection groups 1 and 3, and the single cat from infection group 2 that developed clinical keratitis (FIG. 13). Positive staining was primarily localized to the basal corneal epithelium and anterior corneal stroma in tissues collected on study day 7. Positive staining was localized to the corneal stroma only in tissues collected on study days 14 and 21. This staining was primarily within the anterior and mid-corneal stroma, with fewer organisms within the deep stroma. Positive immunohistochemical staining was not detected in tissues from cats in control groups 4 and 5, or the 2 cats from infection group 2 that did not develop clinical ocular disease. The frequency of amoeba detection by immunohistochemistry was significantly (P=0.007) higher in the infection groups (7 of 9 cats) than the control groups (0 of 6 cats).

Feline herpesvirus-1 PCR and Aerobic Bacterial Culture—All feline herpesvirus-1 PCR assays were negative. Aerobic bacterial cultures were positive for 1 or more organisms in 6 samples from cats in the infection group and 2 samples from cats in the control groups. The frequency of positive bacterial cultures was not significantly (P=0.4) different between the infection groups (6 of 18 samples) and the control groups (2 of 12 samples). Cultured bacteria were inconsistent within study groups and individual cats in both infection groups and control groups and included: Klebsiella pneumonia (n=3 isolates), coagulase negative Staphylococcus spp (n=3), Staphylococcus warneri (n=2), Enterococcus spp (n=1) and Corynebacterium spp (n=1). Bacteria isolated from both infection and control groups were similar and consistent with the normal feline extraocular microflora. The results provide no evidence that microbial pathogens other than Acanthamoeba were responsible for the detected ocular lesions.

The number of infection and control cats was selected primarily to provide adequate tissues for analysis at timepoints selected from previous studies of experimental Acanthamoeba keratitis induction in other animal species. Power analysis was also performed to provide statistical justification for the size of each study group. Hall cats in the infection group (n=9 cats) had detectable criteria of successful amoeba keratitis induction (e.g., keratitis, positive culture, positive confocal microscopy exam, positive histopathology) and no cats in the control group (n=6 cats) had these criteria, this difference would have been statistically significant (P=0.0002) with an alpha of 5% and 100% statistical power.

This forgoing disclosure is not limited to the embodiments described and can be implemented by one skilled in the art with some modifications and alterations within the spirit and scope of disclosed embodiments.

What is claimed is:

1. A pathological animal model for studying a pathological condition of keratitis, made by the process of:

performing a corneal abrasion on a disease-free, feline species;

followed by performing a corneal inoculation for about 18 hours to about 7 days by (a) irrigating the abraded cornea of the feline with about $6\times10^5$ to about $6\times10^6$ Acanthamoeba and/or (b) applying an Acanthamoeba-laden, contact lens to the eye of the feline having a corneal abrasion.

2. The pathological animal model of claim 1, wherein said *Acanthamoeba* is selected from the group consisting of *A. castellanii, A. commandoni, A, culbertsoni, A. divionensisi, A. echinulata, A. griffin, A. hatchetti, A. healyi, A. jacobsi, A. lenticulata, A. lugdunensis, A. mauritaniensis, A. palestinensis, A. pearcei, A. polyphaga, A. pustulosaf, A. quina, A. rhysodes, A. royreba, A. stevensoni, A. triangularis, A. tubiashi*, or a combination thereof.

3. The pathological animal model of claim 1, wherein said pathological condition emulates a condition associated with *Acanthamoeba* keratitis in a human.

4. The pathological animal model of claim 1, wherein said pathological condition is a disruption in a corneal epithelium.

5. The pathological animal model of claim 4, wherein said disruption is a corneal epithelial irregularity, an epithelial ulcer, an stromal infiltrate, a stromal ulcer, a radial keratoneuritis, a keratomalacia, a limbititis, perineuritis, a corneal microcysts, a punctate keratopathy, a bullous keratopathy, a disciform stromal keratitis, pseudodendritic keratitis, an anterior uveitis, a granulomatous stromal reaction, a stromal ring infiltrate formation, a conjunctivitis, a keratitis, a mucopurulent ocular discharge, an intermittent blepharospasm, a moderate conjunctivitis, an axial corneal edema, a multifocal linear anterior stromal leukocyte infiltration, a superficial corneal ulceration, a blepharitis, scleritis, a cataract, a chorioretinitis, a corneal stromal abscess, or a combination thereof.

6. The pathological animal model of claim 1, wherein said feline is a domesticated or a wild eat.

7. The pathological animal model of claim 1, wherein said animal is pathogen free prior to said corneal inoculation of said *Acanthamoeba* in a suspension.

8. A method for screening a therapeutic compound for preventing or treating a symptom for *Acanthamoeba* induced complication comprising: (a) providing an animal model of claim 1, wherein in said animal model one eye serves as a test eye and the other eye serves as a control eye, (b) inoculation of the test and the control eyes with *Acanthamoeba*, (e) administering the therapeutic compound to the test eye, (d) maintaining the test eye and the control eye under conditions appropriate for development of at least one *Acanthamoeba* induced complication in the control eye; (e) assessing said at least one *Acanthamoeba* induced complication in the test eye and the control eye; and, (f) comparing the severity and/or onset of the *Acanthamoeba* induced complication in the test eye with that of the control eye, wherein reduced severity and/or delay in the onset of the *Acanthamoeba* induced complication in the test eye indicates that the candidate agent is the therapeutic agent useful for treating or preventing the *Acanthamoeba* induced complication.

9. The method of claim 8, wherein evaluating the effectiveness of the compound in reducing the severity and/or onset of infection or reducing a symptom associated with infection is monitored on an hourly, a daily, a weekly or a monthly basis.

10. The method of claim 8, Wherein the therapeutic compound is administered topically, intraocularly, intracorneally, intracarnerally, systemically or in a combination thereof.

* * * * *